(12) United States Patent
Long, III (10) Patent No.: US 11,410,397 B2
(45) Date of Patent: Aug. 9, 2022

(54) VR CORRECTIONAL OUTREACH SYSTEM

(71) Applicant: Nathaniel Houston Long, III, Mansfield, OH (US)

(72) Inventor: Nathaniel Houston Long, III, Mansfield, OH (US)

( * ) Notice: Subject to any disclaimer, the term of this patent is extended or adjusted under 35 U.S.C. 154(b) by 0 days.

(21) Appl. No.: 17/240,239

(22) Filed: Apr. 26, 2021

(65) Prior Publication Data

US 2021/0343086 A1 Nov. 4, 2021

Related U.S. Application Data

(60) Provisional application No. 63/017,084, filed on Apr. 29, 2020.

(51) Int. Cl.
| | | |
|---|---|---|
| *G06T 19/00* | (2011.01) | |
| *G09B 5/06* | (2006.01) | |
| *G16H 80/00* | (2018.01) | |

(52) U.S. Cl.
CPC .............. *G06T 19/006* (2013.01); *G09B 5/06* (2013.01); *G16H 80/00* (2018.01)

(58) Field of Classification Search
CPC .......... G06T 19/006; G09B 5/06; G09B 5/12; G16H 80/00; G16H 20/70; G06Q 10/10
See application file for complete search history.

(56) References Cited

U.S. PATENT DOCUMENTS

| | | | | |
|---|---|---|---|---|
| 2018/0240275 A1* | 8/2018 | Clements | .............. | G06T 19/006 |
| 2019/0104324 A1* | 4/2019 | Han | ..................... | H04N 21/234 |

FOREIGN PATENT DOCUMENTS

| | | | |
|---|---|---|---|
| CN | 102354431 A | * | 2/2012 |
| CN | 202153258 U | * | 2/2012 |

OTHER PUBLICATIONS

Shunichi Kasahara and Jun Rekimoto, JackIn Head: Immersive Visual Telepresence System with Omnidirectional Wearable Camera for Remote Collaboration, Nov. 2015, In Proceedings of the 21st ACM symposium on virtual reality software and technology (pp. 217-225). (Year: 2015).*

(Continued)

*Primary Examiner* — Jeffery A Brier
(74) *Attorney, Agent, or Firm* — Brennan, Manna & Diamond, LLC (57) ABSTRACT

This present invention relates to a virtual reality (VR) based outreach program operational using a VR headset and a 360-degree camera. The VR outreach program enables the incarcerated or detained individuals to connect with their families, friends and other interested individuals and allows them to witness birthdays, sporting events, and other events, while spending time in a correctional or detention facility. The VR outreach program ensures the inmates, prisoners or detainees can reach their family, friends and others thereby helping their family and others to adjust to the absence of the incarcerated or detained individual. Also, the outreach program provides a unique way of overcoming the effects incarceration and prevents the inmates or detainees from developing mental illness due to prolonged periods of solitary or isolated confinement.

20 Claims, 3 Drawing Sheets

(56) References Cited

OTHER PUBLICATIONS

Shunichi Kasahara, Shohei Nagai, and Jun Rekimoto, JackIn Head: Immersive Visual Telepresence System with Omnidirectional Wearable Camera, Dec. 2016, IEEE transactions on visualization and computer graphics vol. 23, No. 3, pp. 1222-1234.(Year: 2016).*

Gun A. Lee, Theophilus Teo, Seungwon Kim and Mark Billinghurst, Mixed Reality Collaboration through Sharing a Live Panorama, Nov. 2017, SIGGRAPH Asia 2017 Symposium on Mobile Graphics & Interactive Applications, pp. 1-4. (Year: 2017).*

Gun A. Lee, Theophilus Teo, Seungwon Kim and Mark Billinghurst, A User Study on MR Remote Collaboration Using Live 360 Video, 2018, 2018 IEEE International Symposium on Mixed and Augmented Reality (ISMAR), pp. 153-164. (Year: 2018).*

Theophilus Teo, Louise Lawrence, Gun A. Lee, Mark Billinghurst, and Matt Adcock, Mixed Reality Remote Collaboration Combining 360 Video and 3D Reconstruction, May 2019, In Proceedings of the 2019 CHI conference on human factors in computing systems, pp. 1-14. (Year: 2019).*

\* cited by examiner

VR CORRECTIONAL OUTREACH SYSTEM

CROSS-REFERENCE TO RELATED APPLICATION

The present application claims priority to, and the benefit of, U.S. Provisional Application No. 63/017,084, which was filed on Apr. 29, 2020 and is incorporated herein by reference in its entirety.

FIELD OF THE INVENTION

The present invention relates generally to the field of virtual reality-based systems. More specifically, the present invention relates to a virtual reality-based correctional system that provides a virtual reality outreach program that enables offenders, suspects, detainees or those that have been incarcerated or otherwise detained to interact with their families, relatives, friends or others in a virtual reality ("VR") setting. The system includes a VR headset and a 360-degree camera to operate the system, wherein the system provides an interactive experience to a user. The system ensures that an inmate or other individual can easily reach his or her family, thereby helping the family and other loved ones to adjust to the absence of the individual or the family member depending upon the perspective of the user. Additionally, the system allows inmates to still play a major role in their families' and others lives, such as witnessing or virtually participating in birthdays, sporting events, holidays and more. The VR system of the present invention may also be used by other individuals, such as medical professionals, clergy, educators, vocational trainers, etc., that may play an important role in the well-being of the inmate. Accordingly, the present disclosure makes specific reference thereto. Nonetheless, it is to be appreciated that aspects of the present invention are also equally applicable to other like applications, devices and methods of manufacture.

BACKGROUND OF THE INVENTION

By way of background, a large number of people are incarcerated for committing crimes, and the total number of those incarcerated continues to increase over time. Countries such as the United States have an incredibly high number of incarcerated individuals, as do China, Brazil, the Russian Federation, India and others. In addition, due to immigration related activities, others are being held in detention or deportation centers awaiting resolution or a decision on their case. When an individual is incarcerated for committing a crime or an offence, or is otherwise held while awaiting trial or a hearing on their current predicament, the individual is isolated and has very little interaction with family members, friends, loved ones, etc. Therefore, incarceration has immediate adverse effects on the individual being incarcerated as well as their families, friends and loved ones. For these individuals, some immediate impacts of such isolation include feelings of shame, social stigma, loss of financial support, weakened ties to family and friends and other issues which can lead to psychological stress and illness. The inmates also suffer from various effects due to the incarceration which include lack of affection, missing family gatherings, decreased communication with family and friends and more. Therefore, many inmates will miss their families and friends, and may be unable to play an active role in their lives.

These incarceration effects not only impact the physical health of the inmates, but also can negatively affect their mental health. The stress levels among the offenders, detainees and others in confinement rises due to separation from their families and other individuals that they may be close to for long periods of time and a lack of connected with these individuals. People may lose the ability to communicate with their families, friends and others in order to share their emotions, feelings and other important information which eventually can lead to mental and other health issues among the inmates. Also, due to confinement in prisons, inmates most likely develop mental health issues as a result of the extreme isolation and separation from their prior life outside of the correctional facility. Studies have shown that solitary confinement increases the risk of panic, insomnia, paranoia, aggression and depression. Further, the offenders, detainees or inmates might lose hope while being incarcerated for a long period of time, and may be unable to cope with others or the significant societal changes they face upon release from incarceration.

According to the American Psychological Association, 64% of jail inmates, 54% of incarcerated individuals in state prison, and 45% of incarcerated individuals in federal prison report some form of mental health concerns. Irrespective of the large number of inmates reporting mental health and other concerns, the inmates may be unable to receive proper medication and treatment due to the lack of available funds in the prisons or other issues relating to accessibility.

The prisons, detention centers and other correctional facilities may offer various kinds of recreational programs and services for the inmates or those subject to confinement to aid in overcoming the feelings of depression, anxiety, attention deficit hyperactivity disorder and other mental health issues. Other treatment activities may include work, educational, therapeutic, recreational, and community activities for the inmates and other individuals. However, none of the currently offered programs and services enable the inmates to connect with their family members, friends or others with whom they may be close, to help overcome the incarceration effects.

Therefore, there exists a long felt need in the art for a correctional program for those incarcerated that enables the incarcerated individual to connect with his or her family, friends and others that may provide assistance in the individual's rehabilitation and physical and mental well-being. There is also a long felt need in the art for a correctional program that enables or allows the incarcerated individual to witness important life events with their families and friends including, without limitation, birthdays, sporting events, holidays and other activities, while remaining incarcerated. Additionally, there is a long felt need in the art for a correctional or other remedial program which reduces the likelihood that the incarcerated individual will suffer from mental health issues related to his or her isolation and time away from the family unit and/or the individual's circle of friends. Moreover, there is a long felt need in the art for a correctional or other assistance program which prevents the inmates or other individuals from being adversely impacted by prolonged solitary confinement. Finally, there is a long felt need in the art for a VR correctional outreach system that is relatively inexpensive to manufacture and that is both safe and easy to use.

The subject matter disclosed and claimed herein, in one embodiment thereof, comprises a system for providing virtual reality interaction between a first person and a second person. The system includes an augmented reality or virtual reality (AR/VR) mobile application that may be installed in a mobile computing device of the first person, an AR/VR headset configured to be worn by the second person, and at least one 360 degree camera to record an immersive video. During use, the first person records an immersive video using the AR/VR mobile application and the 360 degree camera, and the second user can view the recorded or live immersive video of the first person via an AR/VR headset in a virtual reality space. The virtual reality space may also be real or created depending on the preferences and/or circumstances that the users wish to create. The second person can be a prisoner, inmate or other incarcerated individual, and the first person can be a family member, relative, doctor, physiotherapist, instructor, clergy member, friend or another individual that may help the second person, or any combination of individuals that may co-develop or provide content or videos. Alternatively, the roles may be reversed, wherein the prisoner, inmate or other incarcerated individual is the first person. The VR system of the present invention allows inmates, prisoners and other incarcerated individuals to continue to play a major role in their families' or friends' lives, and/or to participate in the outside community through virtual reality while continuing to be incarcerated.

In this manner, the novel VR correctional outreach system of the present invention accomplishes all of the forgoing objectives, and provides a relatively easy, convenient and effective solution for enabling incarcerated individuals to interact with their families or community in a virtual reality setting, and ensures that an incarcerated individual can reach those that are important to him or her, thereby helping the inmate and their family or other individuals to mitigate the detrimental effects of long-term incarceration and/or confinement. The VR correctional outreach system of the present invention is also user friendly, as it allows the inmate to play a major role in their families' lives and the lives of other individuals who are important to them through virtual reality, without the risk of physically releasing an incarcerated individual back into society before the completion of his or her sentence.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a system for providing virtual reality interaction between a first person and a second person who is typically at a remote location or otherwise generally inaccessible to the first person. The system comprises an augmented reality/virtual reality (AR/VR) mobile application that is installed in a mobile computing device of the first person, and an AR/VR headset or eyeglasses which are configured to be worn by the second person. At least one 360 degree camera and microphone is also provided to record an immersive video and related audio. In use, the first person records an immersive video using the AR/VR mobile application and the 360 degree camera/microphone. The second user can then view the recorded or live immersive video of the first person via a separate AR/VR headset in a virtual reality space. The virtual reality space can be an arbitrary or other background, which may prove beneficial in treating the second person, or at least minimizing the negative effects typically associated with long term incarceration and/or confinement. The second person can be a prisoner, inmate or other incarcerated individual, and the first person can be a family member, doctor, clergy member, educator, trainer, physiotherapist, friend or the like of the incarcerated individual. The system allows inmates, prisoners and other individuals that are incarcerated to continue to play a major role in their families' lives, or the lives of other individuals important to them, through virtual reality.

In yet a further embodiment of the present invention, a method for providing a virtual reality interaction between an incarcerated person and one or more family or community members or friends of the inmate is disclosed. The method comprises the steps of installing a virtual reality application on a smartphone of the family member or friend, and then recording a least one 360 degree video using one or more 360 degree cameras. Next, the family member or friend uploads the video to the application or to a webpage, along with the time, date, inmate information of whom will view the video, etc. Then, the uploaded video is viewed by the prisoner using an AR/VR headset, glasses or other AR/VR device, thereby allowing the incarcerated individual to continue to interact with loved ones and play a role in their lives. The method may include the additional step of authorizing one or more of the family member or friends before uploading the created video. In the event that the video is not authorized, then the correctional or detention facility officer can suggest or provide edits to the video or other content. Additionally, the method may further verify the prisoner information submitted to the virtual reality application, wherein the AR/VR headset can be a VR helmet or VR glasses.

In yet a further embodiment, a non-transitory, machine-readable medium is provided that has instructions stored thereon. The instructions, when executed by a processor, cause a mobile computing device to operatively couple with one or more 360 degree cameras to record a virtual reality video. A display for a user interface to upload an immersive video created by a user of the computing device is also included, wherein the video may be displayed in a non-immersive, semi-immersive and fully immersive manner using VR glasses or a headset configuration.

The system, application and method of the present invention provides correctional and other confinement or detention facilities with a virtual reality outreach program that enables offenders or those being detained or otherwise confined the opportunity to interact with their families, friends, community members, clergy members, educators and other facilitators in a VR setting, and ensures that an inmate or other detainee can reach their family and friends, thereby helping the family and others adjust to the absence of a family member and vice versa. The prisoner or detainee is provided with a VR headset and/or glasses to view the video, and the virtual reality mobile application or website helps offenders or detainees adjust to their incarceration and potential return to society.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE INVENTION

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for a correctional program that enables an incarcerated individual to connect with his or her family, friends and others that may provide assistance in the individual's rehabilitation and physical and mental well-being. There is also a long felt need in the art for a correctional program that enables or allows the incarcerated individual to witness important life events with their families and friends including, without limitation, birthdays, sporting events, holidays and other activities, while remaining incarcerated. Additionally, there is a long felt need in the art for a correctional or other remedial program which reduces the likelihood that the incarcerated individual will suffer from mental health issues related to his or her isolation and time away from the family unit and/or the individual's circle of friends. Moreover, there is a long felt need in the art for a correctional or other assistance program which prevents the inmates or other individuals from being adversely impacted by prolonged solitary confinement. Finally, there is a long felt need in the art for a VR correctional outreach system that is relatively inexpensive to manufacture and that is both safe and easy to use.

The present invention, in one exemplary embodiment, is a novel system for providing a virtual reality interaction between a first person and a second person and comprises an augmented reality/virtual reality (AR/VR) mobile application that is installed in a mobile computing device of the first person. An AR/VR headset which is sized and configured to be worn by the second person is also provided as part of the system. During use, at least one 360-degree camera is used to record an immersive video, wherein the first person records an immersive video using the AR/VR mobile application and the 360 degree camera. The second user can then view the recorded or live immersive video of the first person via an AR/VR headset in a virtual reality space. The second person can be a prisoner or other incarcerated individual, and the first person can be a family member, doctor, physiotherapist, friend, clergy member, educator or another interested person of the second person, or vice versa. The system allows inmates, prisoners and detainees to continue to play a major role in their families' and other interested persons' lives through virtual reality, wherein the incarcerated individual can still witness birthdays, sporting events, holidays, and other activities while being in the prison, correctional facility or other detainment center.

Figure 1:
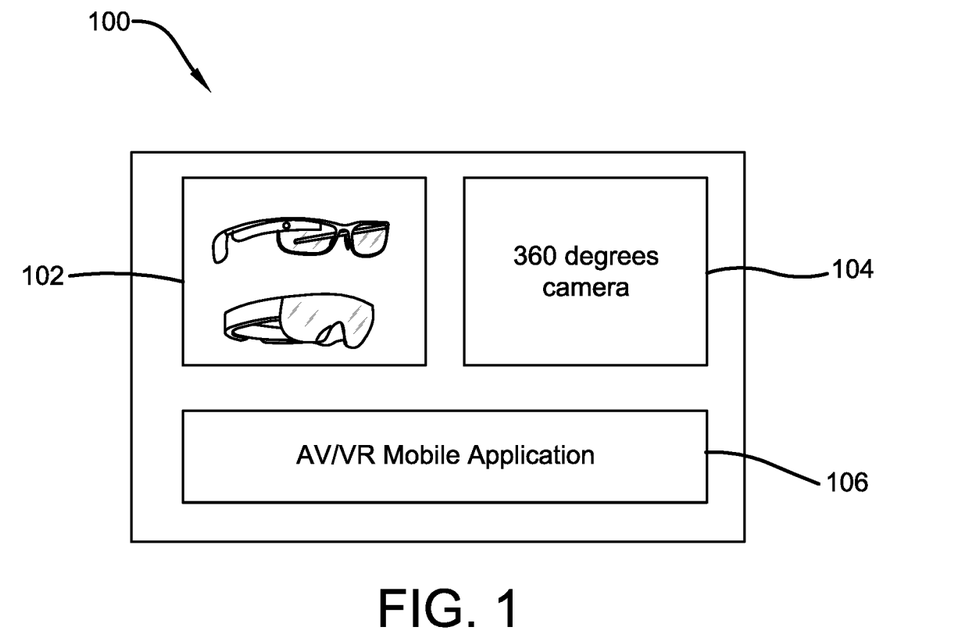
FIG. 1 illustrates a block diagram showing the primary components of one potential embodiment of the Virtual Reality or Augmented Reality (AR/VR) correctional outreach system of the present invention in accordance with the disclosed architecture.

Referring initially to the drawings, FIG. 1 illustrates a block diagram showing the primary components of one potential embodiment of the Virtual Reality or Augmented Reality (AR/VR) correctional outreach system 100 of the present invention in accordance with the disclosed architecture. The AR/VR system 100 is comprised of an AR/VR headset or glasses 102 that can be worn by a prisoner, inmate or detainee, at least one 360 degree camera 104 and an AR/VR mobile application 106. The AR/VR headset 102 can be any conventional headset or glasses that are capable of providing an immersive experience to the prisoner or detainee that is wearing the headset or glasses 102. The AR/VR mobile application 106 is installed on a smartphone, tablet, computer or other suitable electronic device of a family member or a friend of the prisoner or detainee and enables the user to connect to the prisoner or detainee. At least one 360 degree camera 104 is preferably installed at a location of the family or friend to capture 360 degrees videos that may then be streamed or recorded and transmitted to or played on the AR/VR headset 102 worn by the prisoner or detainee during his or her incarceration.

The AR/VR mobile application 106 connects to the internet using a wireless module on a smartphone and is used to transmit a live or recorded 360-degree video to the AR/VR headset 102. The AR/VR mobile application 106 authenticates the family or friend and allows transmission of video and audio after authentication and authorization. In the event the video is not authorized, then the correctional or detention facility officer can suggest or provide edits to the video or other content so that the same may be authorized without violating the rules of the correctional facility. If the video is both authenticated and authorized, the prisoner or detainee wears the AR/VR headset or glasses 102 to view the transmitted video or alternatively, the detainee can view the video through an AR/VR supporting smartphone.

Importantly, the system 100 may also be used in the reverse, wherein the prisoner or detainee uses the AR/VR mobile application 106 along with 360-degree cameras 104 to create and transmit immersive, non-immersive and semi-immersive videos to send to friends and family which can be viewed by them in their AR/VR application or through AR/VR headset 102 after the same have been authenticated and authorized in the manner described above. The AR/VR system 100 of the present invention can also be used to transmit special 3D AR messages, 3D images, videos and text, video and audio calls in a secure manner between prisoners or detainees and their loved ones to help all parties cope with the negative impacts of the incarceration, and to allow the incarcerated individual to still play a major role in the lives of his or her family, friends and other interested persons.

The AR/VR headset 102 can be any wearable smart glasses, headset or smart device that can be positioned over the eyes and/or ears of the individual with an immersive display and related audio to provide the user with a complete immersive, semi-immersive, non-immersive and shared experience. In this manner, the incarcerated individual and his or her family and friends can witness birthdays, celebrations, holidays and other activities by creating and transmitting videos and other messages with the AR/VR mobile application 106. The AR/VR application 106 can also help in significantly reducing the number of repeat offenses, suicides and re-incarceration rates of the incarcerated individual by allowing the individual to connect with friends, family and others to receive the love and support that the individual needs to be rehabilitated and productively returned to society following the completion of his or her incarceration.

The AR/VR mobile application 106 can also be used by doctors, in-prison educators, vocational trainers, clergy members and drug-abuse counselors to prepare education, training and consultation videos, quizzes and other activities which can create a shared experience for the prisoners or detainees. In this regard, the AR/VR system 100 is particularly advantageous during the time of a pandemic, when prisoners or detainees cannot participate in physical or in-person learning programs. The AR/VR mobile application 106 can also be used by the prison authorities, government, detention personnel and other rehabilitation programs to improve the mental well-being of the prisoners and detainees, and to reward good behavior during incarceration by providing incarcerated individuals with an opportunity to interact with their families, other interested persons and friends in a virtual reality setting. It should be appreciated that a webpage can offer the same functionality as the smartphone application, and can provide a similar user interface.

Figure 2:
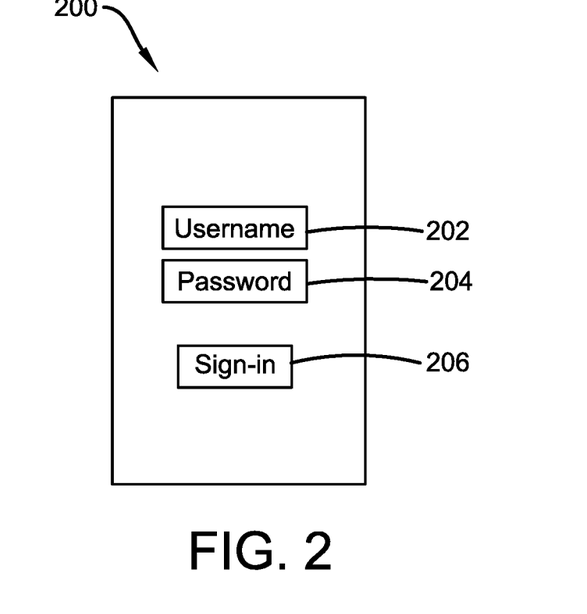
FIG. 2 illustrates a diagrammatic view of one potential embodiment of the home page of the AR/VR correctional outreach system of the present invention in accordance with the disclosed architecture, as would be seen by an incarcerated individual.

FIG. 2 illustrates a diagrammatic view of one potential embodiment of the entrance or home page 200 of the AR/VR correctional outreach system 100 of the present invention in accordance with the disclosed architecture, as would be seen by an incarcerated individual. As noted above, the AR/VR mobile application 106 of the present invention can be used by both prisoners or detainees and their families or friends to create immersive, semi-immersive or non-immersive videos and other content with the help of one or more 360-degree cameras 104. The AR/VR application 106 can be downloaded from an application store or a VR app store and can be paired with any conventional 360-degree camera 104.

To start using the AR/VR application 106 and creating and/or viewing the virtual videos, a user (referring to both recipient and sender, e.g., prisoner and/or friend/family) logs into the application 106 using a sign-in header 206. The user has to also successfully enter in a correct user name using a user name header 202 and a password using a password header 204 when prompted on the home page 200 to enter into the application 106. The smartphone application 106 may also geotag the video along with customization by adding text, songs, images etc. The application 106 allows the prisoners or detainees to see their family and other interested individuals in a virtual reality setting, which provides a more realistic and personal feel than a traditional phone call or video messaging.

Figure 3:
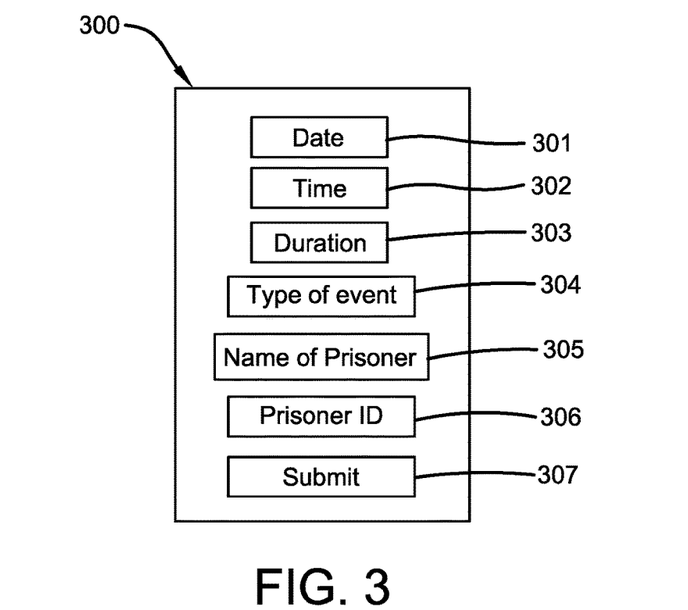
FIG. 3 illustrates a diagrammatic view of one potential embodiment of the home page of the AR/VR correctional outreach system of the present invention in accordance with the disclosed architecture, as would be seen by a family member, friend of other loved one of the incarcerated individual.

FIG. 3 illustrates a diagrammatic view of one potential embodiment of the home page 300 of the AR/VR correctional outreach system 100 of the present invention in accordance with the disclosed architecture, as would be seen by a family member, friend of other loved one of the incarcerated individual. As shown, the home page 300 of the AR/VR application of a family or friend provides the user with options that can be selected to configure a time for the prisoner or detainee to watch a video or other provided content of the family, friend or other interested party. For example, a date 301 and a time 302 may be initially selected by the family member or friend, as well as a duration 303 of the video, which can be, for example, 5 mins, 10 mins, 15 mins or any other suitable time increment that complies with the rules of the correction facility. A type of event 304 may also be selected to allow the prisoner and detention administrators or authorities know about the event in advance such as, but not limited to, a birthday, celebration, achievement, sports or personal event, etc. of any family member or friend so that the event can be authorized or approved before allowing transmission of the content to the detainee or prisoner or vice versa. This method may also become a parameter for prioritizing the various VR/AR communication requests if a large number of requests are made during a certain period of time or for a particular viewing window of time.

Additionally, the name of a prisoner 305 for which the video, audio or live video is to be organized is required along with prisoner's ID 306. This information enables the authorities at a correctional facility to ascertain whether such an outreach or other program is allowed and/or is suitable for the prisoner or detainee. After inputting all of the required information, the request is submitted to the authorities for approval using the submit button 307. Nonetheless, in an alternative embodiment, approval may not be required, and the prisoner or detainee may be permitted to simply connect with the friend, family or other interested individual on the configured date and time for the scheduled duration.

In a further embodiment of the AR/VR system 100 of the present invention, an automatic notification and/or a reminder may be sent to the prisoner or, alternatively, the authorities at the correctional or detention facility so that all parties are aware and reminded of the upcoming interaction. In yet a further embodiment, a prisoner, detainee or other incarcerated individual may request to create or receive such an interaction using the mobile application 106 of the present invention.

Figure 4:
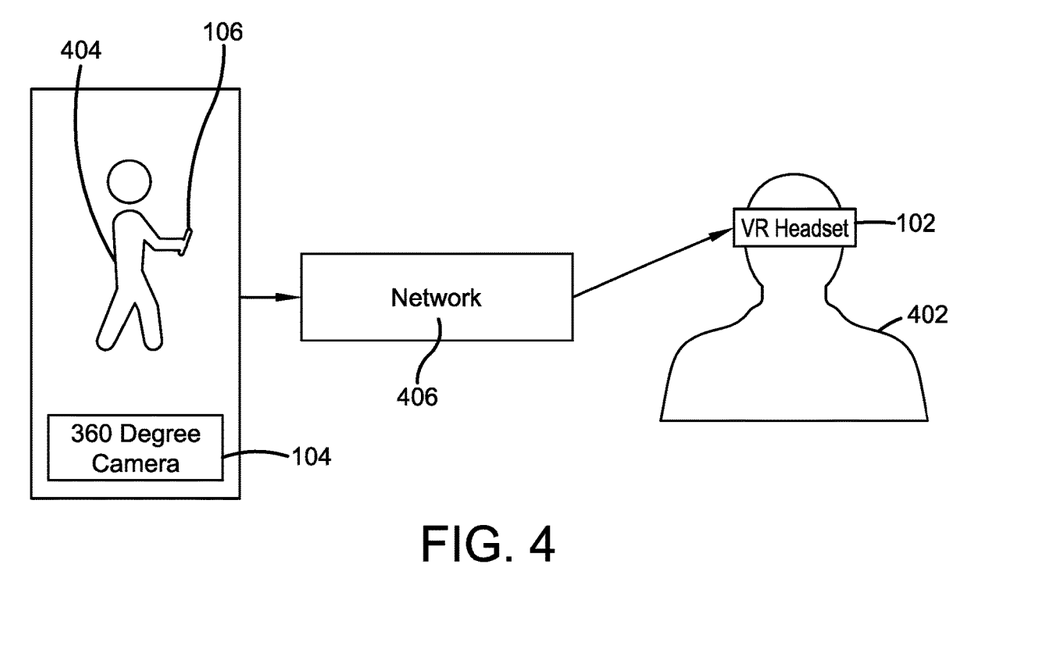
FIG. 4 illustrates a diagrammatic view of one potential embodiment of an interaction between an incarcerated individual and a loved one using the AR/VR correctional outreach system of the present invention in accordance with the disclosed architecture.

FIG. 4 illustrates a diagrammatic view of one potential embodiment of an interaction between an incarcerated individual 402 and a loved one 404 using the AR/VR correctional outreach system 100 of the present invention in accordance with the disclosed architecture. More specifically, the prisoner or detainee 402 wears an AR/VR headset 102 which is in wireless communication with the AR/VR application 106 installed in a smartphone occupied by a family member, friend or other interested individual 404. The family member, friend or other interested individual 404 uses one or more 360-degree cameras 104 to create an immersive, semi-immersive or non-immersive video or other content for the benefit of the prisoner or detainer 402. The smartphone application 106 may connect to the AR/VR device 102 through a public or private network 406, such as the internet. It should be appreciated that in one embodiment of the present invention, an authentication process and background check of the family member, friend or other interested individual 404 may also be performed by the AR/VR system 100 of the present invention to maintain the security of the correctional facility.

A prisoner or detainee 402 can also create immersive, semi-immersive or non-immersive videos using the smartphone application 106 and one or more 360-degree cameras 104 that may be placed in a separate room by the prison or detention facilities authorities. The prisoner or detainee 402 may have to be sent to the room for interacting with the family, friends or other interested individuals, or the same may be accomplished in the room or space of the incarcerated individual 402 if permitted by the correctional facility authorities. A second headset or glasses 102 may also be provided so that a correction officer or other individual may monitor the content of the video or content being recorded or displayed between the incarcerated individual 402 and the family member, friend or other interested individual 404.

Figure 5:
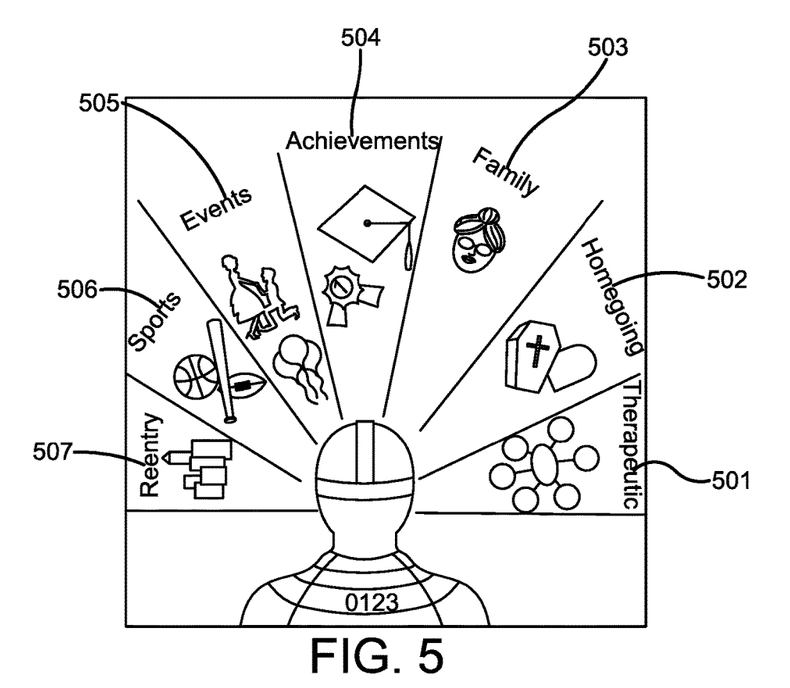
FIG. 5 illustrates a diagrammatic view of one potential embodiment of the various categories of interaction between an incarcerated individual and a loved one using the AR/VR correctional outreach system of the present invention in accordance with the disclosed architecture.

FIG. 5 illustrates a diagrammatic view of one potential embodiment of the various categories of interaction between an incarcerated individual 402 and a loved one 404 using the AR/VR correctional outreach system 100 of the present invention in accordance with the disclosed architecture. As noted above, the AR/VR system 100 of the present invention can also be used by doctors, counselors, physiotherapists, clergy members, educators, vocational specialists and others assisting the inmate or detainee 402 with his or her individual struggle and to provide therapy to have a beneficial effect 501 on the incarcerated individual 402. For example, the incarcerated individual 402 can virtually attend a special ceremony 502 of a loved one, or interact with family 503. If a prisoner or detainee 402 is a parent or guardian, then a live or recorded achievement ceremony 504 of a child or other ward can be virtually viewed by the prisoner or inmate 402. Additional life events 505 such as a marriage, or birthday of a family member or friend can also be attended in a VR setting by the prisoner, detainee or inmate 402 by using the AR/VR system 100 of the present invention, as well as sporting events 506, re-entry events 507, etc.

Figure 6:
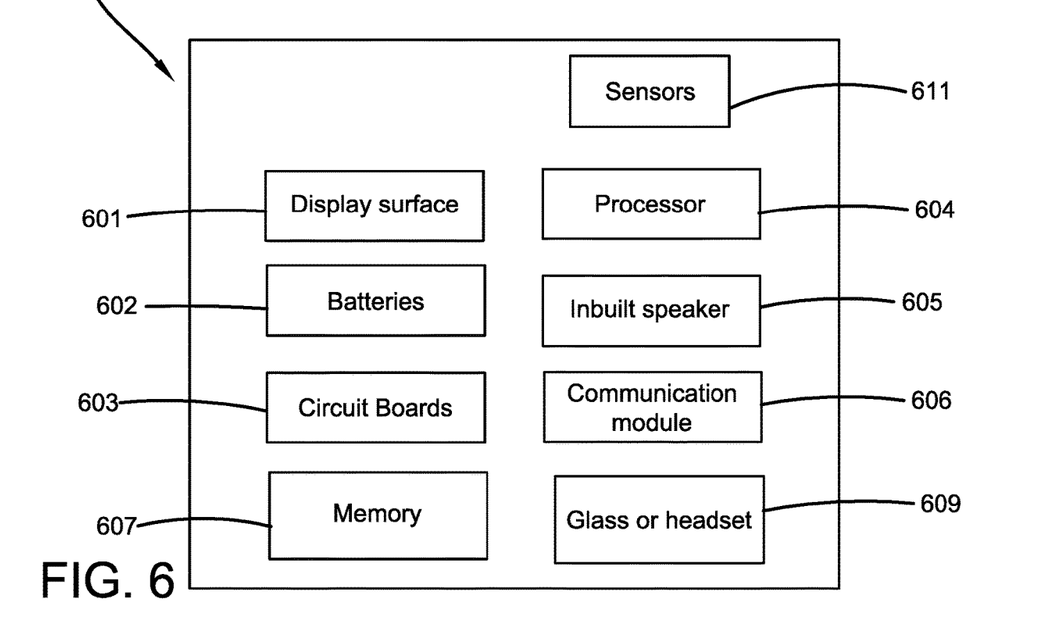
FIG. 6 illustrates a block diagram showing the primary electronic components of one potential embodiment of the Virtual Reality or Augmented Reality (AR/VR) correctional outreach system of the present invention in accordance with the disclosed architecture.

FIG. 6 illustrates a block diagram showing the primary electronic components of one potential embodiment of the AR/VR correctional outreach system 100 of the present invention in accordance with the disclosed architecture. More specifically, the AR/VR device 102 includes a display surface 601 to display the AR/VR video of a family member, friend or other interested individual, wherein it will readily be appreciated by one of ordinary skill in the art that the wearable VR/AR device 102 is not limited to a particular type of device or configuration. The device 102 further comprises rechargeable batteries 602 which may be integral to the device to provide power to the display and other electronic components, and one or more circuit boards 104 that connect all of the electronic components of the device 102 for effective operation. Further, a processor 604 controls the operation of the electronic components of the device 102 by sending instructions to the same, and a memory 607 may be used to provide playback of previously viewed videos or content stored thereon. Each of the components may then be connected to the headset or smart glasses 609.

Additionally, the device further comprises a built-in earphone 605 (with or without an integrated microphone) to enable the user to hear the associated audio of the communication, as well as a wireless communication module 606 that is used to connect the device 102 to the internet or other wireless communication channel (e.g., 5G/LTE, RFID, NFC, Bluetooth, etc.) to enable the communication. The wireless communication module 606 is built into the AR/VR device 102 and is connected to the circuit boards 603. The audio can be provided in real time as well to provide an additional emotional lift or instructions to the individual viewing the video or content, or the same may be prerecorded along with the original video or content. One or more sensors 611 may also be included with the device 102 to collect data about the responses of the individual watching the video or content and obtained from the head set 609.

The smartphone or mobile computing device upon which the AR/VR smartphone application 106 is installed may further comprise a touch-input controller that can include one or more input devices, output devices and/or sensors. The input devices can include, but are not limited to, a touch surface or screen, a camera, and a microphone, and can cause a particular action to occur in a VR space. The output devices may include, but are not limited to, a display and speakers that can provide feedback and/or output to a user of the smartphone, wherein the feedback and/or output can be an combination of visual, tactical or audio.

In one embodiment, the present invention includes a method for providing a virtual reality interaction between a prisoner, inmate or detainee and one or more family members or friends. The method includes a friend or family member installing the AR/VR application 106 on a smartphone, recording 360 degree videos using one or more 360 degree cameras 104, inputting the prisoner or detainee information into the application or corresponding webpage and uploading the video to the application or to the webpage. The incarcerated individual then views the uploaded video using an AR/VR headset device 102 after the same has been authenticated and authorized by the appropriate individuals at the correctional facility, thereby allowing the incarcerated individual to continue to play a major role in the lives of their family and friends.

Additionally, various VR applications such as, but not limited to, a movie, game or a virtual tour of a prison, detention center or other confinement facility to which the prisoner, detainee or inmate is to be moved can be executed on the AR/VR headset 102. The AR/VR headset 102 further comprises circuitry to execute the VR application and to render or create a computer-generated, 3D environment (a VR space) so that the family members, friends and other interested individuals can interact with the incarcerated individual.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "virtual reality interaction system", "Augmented Reality/Virtual Reality (AR/VR) system", "interaction system", and "system" are interchangeable and refer to the VR correctional outreach system 100 of the present invention.

Notwithstanding the forgoing, the VR correctional outreach system 100 of the present invention and its various components can be of any suitable size and configuration as is known in the art without affecting the overall concept of the invention, provided that it accomplishes the above stated objectives. One of ordinary skill in the art will appreciate that the size, configuration and material of the VR correctional outreach system 100 and its components as shown in the FIGS. are for illustrative purposes only, and that many other sizes and shapes of the VR correctional outreach system 100 are well within the scope of the present disclosure.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A remedial system for use in a correctional or detention facility, the remedial system comprising:
   a headset sized and configured for use by a first individual;
   a mobile application installed on a mobile device for recording an event, the mobile application downloaded by a second individual that is remote from the first individual and configured to authenticate both the first and second individuals;
   an authorization sequence provided by the correctional or detention facility;
   at least one 360 degree camera; and
   a virtual reality video or other content created by the second individual using the at least one 360 degree camera, wherein the headset is used to view the virtual reality video or other content at the correctional or detention facility; and
   wherein the authorization sequence is configured to allow the correctional or detention facility to authorize or not authorize viewing of the virtual reality video or other content by the first person, and if not authorized, to provide feedback to facilitate authorization.

2. The remedial system as recited in claim 1, wherein the first individual is incarcerated at the correctional or detention facility.

3. The remedial system as recited in claim 1, wherein the second individual is one of a family member, a relative, a doctor, a psychotherapist, an instructor, a clergy member, a friend, an educator, a trainer, a vocational instructor or a combination thereof to the first individual.

4. The remedial system as recited in claim 3, wherein the second individual creates the virtual reality video or other content.

5. The remedial system as recited in claim 1, wherein the first individual is incarcerated at the correctional or detention facility and the second individual is a family member, a friend or an interested person of the first individual.

6. The remedial system as recited in claim 1 further comprising a transmission module for transmitting the video or content from the second individual to the first individual.

7. The remedial system as recited in claim 1 further comprising a memory for storing the virtual reality video or other content.

8. The remedial system as recited in claim 1 further comprising a sensor for recording a reaction of the first individual to the virtual reality video or other content.

9. The remedial system as recited in claim 1 further comprising a user display for use by the second individual to make a selection and provide an instruction for creating the virtual reality or other content.

10. The remedial system as recited in claim 1 further comprising a wireless communication module for creating a real time communication between the first individual and the second individual.

11. The remedial system as recited in claim 1 further comprising a second 360 degree camera for creating the virtual reality video or other content.

12. The remedial system as recited in claim 1, wherein the remedial system provides one of a full immersion, a semi-immersion or a non-immersion content.

13. A method of using a virtual reality system to communicate with an incarcerated individual comprising the steps of;
   providing the virtual reality system that is comprised of a headset, a smart application, a display, at least one 360 degree camera, a memory and a processor;
   authenticating a content creator to use the smart application;
   using the virtual reality system less the headset to create a virtual reality video or other content;
   transmitting the virtual reality video or other content to an administrative person at a correctional or detention facility for review prior to providing it to an incarcerated individual;
   approving or not approving the virtual reality video or other content;
   providing feedback to facilitate approval if the virtual video or other content is not initially approved;
   authenticating the incarcerated individual to access the virtual reality video or other content; and
   displaying the virtual reality video or other content to the incarcerated individual at the correctional or detention facility if approved.

14. The method as recited in claim 13 comprising a further step of recording a reaction to the virtual reality video or other content received by the incarcerated individual after the step of displaying.

15. The method as recited in claim 13 comprising a further step of enabling a real time communication with the incarcerated individual after the step of displaying.

16. The method as recited in claim 15 comprising a further step of downloading the smart application to a smart device after the step of providing the virtual reality system.

17. The method as recited in claim 13, wherein the step of recording is performed remotely from the step of displaying.

18. The method as recited in claim 13 comprising a further step of modifying the virtual reality video or other content after the step of transmitting.

19. A system for providing assistance to an incarcerated individual, the system comprising:
   a virtual or alternate reality headset or smart glass;

a smart device comprising a mobile application configured to authenticate and allow a non-incarcerated individual to create a video or other content for use by the virtual or alternate reality headset or smart glass;

the video or other content created to provide a display for the virtual or alternate reality headset or smart glass;

a memory for holding the video or other content;

a communication module for allowing communication between the incarcerated individual, the non-incarcerated individual, and a correctional or detention facility;

an authorization sequence configured to allow the correctional or detention facility to approve, not approve, or suggest feedback to facilitate approval or the video or other content; and a processor for retrieving information from the memory for displaying the video or other content to the incarcerated individual if approved.

20. The system as recited in claim 19, wherein the second person is one of a family member, a relative, a doctor, a psychotherapist, an instructor, a clergy member, a friend, an educator, a trainer, or a vocational instructor to the incarcerated individual.

\* \* \* \* \*